(12) United States Patent
Esh et al.

(10) Patent No.: US 10,661,081 B2
(45) Date of Patent: *May 26, 2020

(54) NON-INVASIVE DEVICE AND METHOD FOR TREATING GASTRO ESOPHAGEAL REFLUX DISEASE (GERD) AND THE DIGESTIVE SYSTEM

(71) Applicants: Mordechay Esh, Ramat Gan (IL); Giora Arbel, Tel-Mond (IL)

(72) Inventors: Mordechay Esh, Ramat Gan (IL); Giora Arbel, Tel-Mond (IL)

(73) Assignee: GERDCARE MEDICAL LTD., Yokneam Illit (IL)

( * ) Notice: Subject to any disclaimer, the term of this patent is extended or adjusted under 35 U.S.C. 154(b) by 27 days.

This patent is subject to a terminal disclaimer.

(21) Appl. No.: 15/915,255

(22) Filed: Mar. 8, 2018

(65) Prior Publication Data
US 2018/0214692 A1 Aug. 2, 2018

Related U.S. Application Data

(63) Continuation of application No. 15/132,270, filed on Apr. 19, 2016, now Pat. No. 9,925,375, which is a (Continued)

(51) Int. Cl.
*A61N 1/00* (2006.01)
*A61N 1/36* (2006.01)
(Continued)

(52) U.S. Cl.
CPC ....... *A61N 1/36007* (2013.01); *A61N 1/0452* (2013.01); *A61N 1/0476* (2013.01);
(Continued)

(58) Field of Classification Search
CPC ............ A61N 1/36007; A61N 1/36014; A61N 1/36031; A61N 1/36034; A61N 1/36135;
(Continued)

(56) References Cited

U.S. PATENT DOCUMENTS

| 5,716,385 A | 2/1998 | Mittal et al. |
| 2009/0036938 A1 | 2/2009 | Shipley et al. |

(Continued)

FOREIGN PATENT DOCUMENTS

| CN | 104736197 A | 6/2015 |
| CN | 105848708 A | 8/2016 |

(Continued)

OTHER PUBLICATIONS

Crowell, Implanted electrical devices and gastroesophageal reflux disease: an effective approach to treatment, Expert Rev. Gastroenterol. Hepatol. 7(3), 189-191 (2013) (3 pages).
(Continued)

*Primary Examiner* — Scott M. Getzow
(74) *Attorney, Agent, or Firm* — Mark M. Friedman

(57) ABSTRACT

A non-invasive method and device for treating gastroesophageal reflux disease (GERD) in a patient are disclosed. The method calls for positioning electrodes, and applying electrical symmetrical bursts. In particular, positioning step requires positioning a plurality of electrodes in electrical contact with the skin of a target region of the abdomen of the patient. The application step calls for applying a series of electrical symmetrical bursts to said electrodes. That application step generates contractions of abdominal muscles thereby generating movements of a digestive system of said patient wherein said movements are for causing the content of the esophagus to return to the stomach and to relieve GERD symptoms of said patient.

10 Claims, 8 Drawing Sheets

Related U.S. Application Data continuation-in-part of application No. PCT/IB2014/066721, filed on Dec. 9, 2014.

(51) Int. Cl.
  *A61N 1/04* (2006.01)
  *A61N 1/18* (2006.01)
  *A61N 1/32* (2006.01)

(52) U.S. Cl.
  CPC .............. *A61N 1/0484* (2013.01); *A61N 1/18* (2013.01); *A61N 1/321* (2013.01); *A61N 1/36* (2013.01); *A61N 1/36014* (2013.01)

(58) Field of Classification Search
  CPC .. A61N 1/36178; A61N 1/0484; A61N 1/321; A61N 1/0476; A61N 1/0452; A61N 1/36; A61N 1/18
  See application file for complete search history.

(56) References Cited

U.S. PATENT DOCUMENTS

| | | |
|---|---|---|
| 2011/0004266 A1 | 1/2011 | Sharma |
| 2012/0221073 A1 | 8/2012 | Southwell et al. |
| 2013/0006322 A1 | 1/2013 | Tai |
| 2013/0178912 A1 | 7/2013 | Sharma |
| 2014/0018657 A1 | 1/2014 | Sharma |
| 2014/0135886 A1 | 5/2014 | Cook et al. |
| 2014/0222106 A1 | 8/2014 | Sharma et al. |
| 2014/0257425 A1* | 9/2014 | Arcot-Krishnamurthy ................. A61N 1/36117 607/44 |
| 2014/0316484 A1 | 10/2014 | Edgerton et al. |
| 2015/0057718 A1 | 2/2015 | Sharma et al. |
| 2015/0119646 A1 | 4/2015 | Sharma et al. |
| 2015/0119952 A1 | 4/2015 | Sharma et al. |
| 2015/0297885 A1 | 10/2015 | Goode et al. |
| 2016/0001071 A1 | 1/2016 | Sharma et al. |
| 2016/0030734 A1 | 2/2016 | Sharma et al. |
| 2016/0059010 A1 | 3/2016 | Sharma et al. |
| 2017/0021169 A1 | 1/2017 | Sharma et al. |
| 2017/0128716 A1 | 5/2017 | Goode et al. |
| 2017/0165483 A1 | 6/2017 | Sharma et al. |

FOREIGN PATENT DOCUMENTS

| | | |
|---|---|---|
| CN | 105899256 A | 8/2016 |
| CN | 105939755 A | 9/2016 |
| NZ | 616944 A | 6/2016 |
| WO | 2006113802 A2 | 10/2006 |
| WO | 2016081468 A2 | 5/2016 |

OTHER PUBLICATIONS

Kappelle et al., Electrical stimulation therapy of the lower oesophageal sphincter for refractory gastro-oesophageal reflux disease—interim results of an international multicentre trial; Aliment Pharmacol Ther 2015; 42: 614-625 (12 pages).

Rinsma et al., Effect of Electrical Stimulation Therapy of the Lower Esophageal Sphincter on Postprandial Reflux Mechanisms in GERD Patients, AGA Abstracts Apr. 2016 vol. 150, Issue 4, Supplement 1, p. S478.

Labenz et al., Inadequate Symptom Control on Long-Term PPI Therapy in GERD and Fact or Fiction? (LOPA II Study), AGA Abstracts Apr. 2017vol. 152, Issue 5, Supplement 1, p. S660.

Rodriguez et al., Electrical stimulation therapy of the lower esophageal sphincter is successful in treating GERD: long-term 3-year results, Surg Endosc, published online: Oct. 20, 2015.

Labenz et al., Preliminary Results of a Prospective Multi-Center Observational Registry of Lower Esophageal Sphincter Stimulation for GERD: The Less-GERD Registry, AGA Abstracts Apr. 2016 vol. 150, Issue 4, Supplement 1, p. S478.

Rodriguez et al., Short-term electrical stimulation of the lower esophageal sphincter increases sphincter pressure in patients with gastroesophageal reflux disease, Neurogastroenterol Motil (2012) 24,446—e213.

Rodriguez et al., Two-year results of intermittent electrical stimulation of the lower esophageal sphincter treatment of gastroesophageal reflux disease, Surgery vol. 157, No. 3 Mar. 2015.

Siersema et al., Electrical Stimulation Therapy (EST) of the Lower Esophageal Sphincter (LES) for Refractory GERD—One Year Results of an International Multicenter Trial, AGA Abstracts Apr. 2016 vol. 150, Issue 4, Supplement 1, p. S216.

Iwa et al., "Electroacupuncture at ST-36 accelerates colonic motility and transit in freely moving conscious rats" 2006, American Journal of Physiology—Gastrolintestinal and liver physiology 290, p. G 285.

Zhang et al., "Clinical curative effect of electroacupuncture combined with zhukuanzhong capsules for treating gastroesophageal reflux disease"; Jounrnal of Traditional Chinese Medicine; Sep. 2012, 32(3), pp. 364, 366-368.

\* cited by examiner

NON-INVASIVE DEVICE AND METHOD FOR TREATING GASTRO ESOPHAGEAL REFLUX DISEASE (GERD) AND THE DIGESTIVE SYSTEM

FIELD OF THE INVENTION

The present disclosure relates to medical devices in general, and to medical devices related to digestive system and GERD in particular.

BACKGROUND OF THE INVENTION

Gastroesophageal reflux disease (GERD) is caused by stomach acid coming up from the stomach into the esophagus. The symptoms include abdominal pain, heart burn, asthma, mucosal damage and even cancer. GERD is usually caused by changes in the barrier between the stomach and the esophagus, including abnormal relaxation of the lower esophageal sphincter (LES) (which normally holds the top of the stomach closed), impaired expulsion of gastric reflux from the esophagus, or a hiatal hernia.

Treatment is typically via lifestyle changes and medications such as proton pump inhibitors (PPI), H2 receptor blockers or antacids. Medication therapy is effective up to 60% of the western world population. It is associated with various adverse effects, raising concern about the safety of its long-term use.

Surgical therapy (fundoplication) and endoscopic interventions provide an alternative to patients who do not respond to medication therapy, or are reluctant to use such medications for long periods of time, but it is associated with adverse effects. Various endoscopic intervention methods were developed in the last number of years, however, poor efficacy and complications have limited their use in clinical practice. The efficacy of all surgical interventions is decreasing in time.

U.S. Pat. No. 7,660,636 discloses an electrical stimulation device and method for the treatment of dysphagia. In a preferred embodiment, the electrical stimulation device includes one or more channels of electrodes each of which includes a first electrode positioned in electrical contact with tissue of a target region of a patient and a second electrode positioned in electrical contact with tissue of a posterior neck region or a posterior thoracic region of the patient. A series of electrical pulses are then applied to the patient through the one or more channels of electrodes in accordance with a procedure for treating dysphagia.

U.S. Pat. No. 5,716,385 an electronic pacemaker is used to counter-act crural diaphragm relaxation thereby preventing and/or treating gastroesophageal reflux. The pacemaker can be implantable, or be connected to the skeletal muscles of the crural diaphragm through the skin. A sensor is used to identify spontaneous intermittent relaxations of the diaphragm. During these spontaneous intermittent relaxations, one or more electrodes are used to stimulate the skeletal muscles of the crural diaphragm to cause contraction of the lower esophageal sphincter.

SUMMARY OF INVENTION

Embodiments of the present invention disclose a non-invasive device for facilitating therapy of patient suffering from the gastrointestinal system diseases or symptoms, and in particular suffering Gastroesophageal reflux disease (GERD). The device is a noninvasive device that is positioned by the patient on the skin of the patient abdomen and electrically stimulates the abdomen muscles. This treating results in dynamic motions of the digestive system, which causes the treatment of various digestive symptoms or diseases.

In one embodiment, the device causes an increase of the esophagus motility and strengthens the esophageal sphincter, which releases or suppresses the Gastroesophageal reflux symptoms.

In one other embodiment, the electrical stimulation directs the stomach contents to creep up to the esophagus, causing unpleasant sensation leading to decrease the appetite. The unpleasant sensation occurs when device works both during eating and/or in between meals. The treatment increases the stomach pressure and facilitates the satiation feeling as obesity treatment.

In one other embodiment the electrical stimulation causes the stomach contents to creep down to the duodenum and to empty the stomach. This treatment is effective in case of paralysis of the stomach.

In one other embodiment the electrical stimulation cause the transverses colon contents to creep down to the sigmoid colon as a treatment of constipation. In such a case, two channels stimulation may be used.

The device may be built from a sealed plastic case that contains an electrical circuit and a battery/batteries pack in one embodiment, a pair or more of electrodes coated with conductive adhesive (or hydrogel) or other any type of electrodes are attached to the case. In some other embodiments, some or all of the electrodes are separated from the case to be able to locate the electrodes in various locations of the patient abdomen. The device is integrated with a belt that the patient wears. The stimulation program begins when two or more electrodes are in contact with the skin. The user can control the device by keys on the device or by any remote control facilities.

The device is self-applied for daily use, typically after meal. In order to determine the optimal application location on the patient body and find the device optimal parameters (e.g. amplitude, frequency and burst/pulse sequence, etc.) an initial set up session may be required. This session can be done with a trained clinician or via printed or video user guide.

The stimulation pulses may be monophasic or asymmetrical or symmetric albiphasic in typical rang with a specific time pattern or modulated pattern wherein time pattern or modulated pattern are denoted as a burst and asymmetrical burst is denoted as a current wave form in which the time of ramp up is different from the time of ramp down. Max Voltage range is +300V (typically 200V), max current range is 150 mA (typical 100 mA); pulse frequency range is 10 Hz-100 Hz (typical 20 Hz-4, burst frequency 0.1-10 Hz (typical 0.25 Hz-4 Hz).

In some embodiments, the pulses are synchronized with the patient body signals. For example, the pulses may be synchronized with breathing, heart pulse, monotony movements, and body position. Synchronizing may be done by a sensor that is included in the device. Examples of such sensors are Accelerometer, Gyro, Magnetic Compass, Inclinometer and Respiratory Transducer based on a piezoelectric device (for sensing body position, movements and breathing), ECG amplifiers and microphone (for sensing heart rate).

Breathing, body position and movements changes the stomach and esophagus pressure and position. The synchronization is required for generating optimal pulses only while the abdomen pressure is positive through the inspiration cycles.

One technical problem dealt with by the present disclosure is how to affect motility of the esophagus and stomach system or/and the diaphragm of a patient in a non-invasive way.

One technical solution is to continuously electrically stimulating the abdomen muscles, with specific bursts wherein the frequency and the power of stimulation may be controlled by the patient. The burst rapid ramp up direction may be determined in accordance with the symptom. For example, in the case of Gastroesophageal reflux disease (GERD) a specific current wave forms and treatment protocols cause the effect of creeping materials to the stomach direction for treating GERD patient.

One other technical solution is to create the dynamic motions by a belt that contains a pulse motion mechanism. When the subject wears the belt the mechanism is positioned onto a selected region or regions of the patient abdomen. The mechanism extends and release reciprocally (alternatively inflates and deflates) causing the abdomen wall to follow its movements. The mechanism is activated by a few optional electrical current patterns that are generated by the control unit and synchronized with the patient body signals.

One technical problem dealt with by the present disclosure is how to cause movement of the content of digestive system of a patient in a non invasive way.

One technical solution is to generate asymmetrical movements of the digestive system (like the esophagus) by applying asymmetrical electrical stimulation bursts onto the abdomen muscles, wherein the frequency and the power of stimulation may be controlled by the patient. The asymmetrical bursts generate abdomen muscles asymmetrical contractions. Those contractions generates forward and "fast back" displacement of the esophagus (via the stomach) causing the remaining materials creeping back to the stomach, like in "Vibration Conveyer", wherein the ramp direction is determined in accordance with the desired direction of the digestive system. For example, in the case of Gastroesophageal reflux disease (GERD) a fast ramp direction is upward and the slow phase is downward, causing the content of the esophagus return to the stomach and release the GERD symptoms of the patient.

One other technical problem dealt with by the present disclosure is how to strengthen the esophageal sphincter One other technical solution is electrically stimulating the abdominal muscles. For every burst of stimulation the pressure in the stomach increases causing the esophageal sphincter muscle to contract and to prevent the stomach content entering to the esophagus, numerous times every day. The numerous contractions of the sphincter muscle cause thickening and strengthening of the sphincter which prevent the reflux syndrome in long term.

One other technical problem is how to optimize the stimulation effect. A burst that acts during the abdomen negative pressure cycles it not effective though a burst that acts during the abdomen positive pressure cycles it effective.

One other technical solution is synchronizing the pulses timing with the patient body signals. Breathing, body position and movements changes the stomach and esophagus pressure and position. The synchronization is required for generating optimal pulses only while the abdomen pressure is positive through the inspiration cycles. In another embodiment the device synchronizes the pulses generation with heart beat rate measured by ECG (electrocardiogram) sensor. Pulses are generated during the periods of positive values. In another embodiment body position is performed by Gyro and/or accelerometer sensors.

One exemplary embodiment of the disclosed subject matter is a method for treating gastroesophageal reflux disease (GERD) in a patient. The method comprising: positioning a plurality of electrodes, in electrical contact with the skin of a target region of the patient abdomen; and applying a series of electrical bursts to the electrodes wherein the electrical bursts are adapted for electrically stimulating the abdomen muscles of the patient in the target region; thereby causing the esophageal contents to creep down to the stomach.

According to some embodiments the method further comprising applying a series of electrical asymmetric bursts to thereby generating asymmetrical contractions of the muscles; wherein a direction of a fast phase of the bursts being upward and a direction of a slow phase of the bursts being downward; thereby generating movements of a digestive system of the patient; wherein the movements being for causing the content of the esophagus to return to the stomach and to release the GERD symptoms of the patient. According to some embodiments the method further comprising synchronizing the pulses with the patient body signals. According to some embodiments the body signals comprise one member of a group consisting of breathing, heart pulse, monotony movements and body position.

One other exemplary embodiment of the disclosed subject matter is a non-invasive device for treating the digestive system symptoms of a patient; the device comprises: a plurality of electrodes adapted to be placed in electrical contact with the skin of the abdomen; a pulse generator 107 for providing asymmetric bursts electrical stimulation to the electrodes; wherein the asymmetric bursts being for stimulating the abdomen muscles for a moving the digestive system; wherein the moving being for treating a digestive symptom or a diseases; a control unit 103 for controlling the pulse generator 107 wherein maximum voltage range of the pulse being +300V, maximum current range being 150 mA; pulse frequency range being 10 Hz-100 Hz and burst frequency being 0.1-10 Hz a sensor connectable to the control unit adapted for sensing body-signals from the patient; wherein the control unit is further adapted for synchronizing the pulse generator 107 in accordance with the body-signals to thereby improving the effect of the electrical stimulation.

According to some embodiments the device digestive system symptoms being one member of a group consisting of reflux, obesity and constipation. According to some embodiments the pulse generator 107 is configured to determine the pulse ramp up direction in accordance with the desired direction. According to some embodiments the sensor being one member of a group consisting of a Piezoelectric Respiratory Belt Transducer for sensing breathing rate, an ECG for sensing heartbeat, a Gyro and accelerometer for sensing body movements.

One other exemplary embodiment of the disclosed subject matter anon-invasive device for treating gastroesophageal reflux disease of a patient; the device comprises: a plurality of electrodes adapted to be placed in electrical contact with the skin of the abdomen; a pulse generator 107 for providing asymmetric electrical stimulation bursts to the electrodes; wherein the asymmetric electrical stimulation bursts being for generating asymmetrical contractions of the muscles; wherein a direction of a fast phase of the bursts being upward and a direction of a slow phase of the burst being downward; thereby generating movements of a digestive system of the patient; wherein the movements being for causing the content of the esophagus to return to the stomach and to release the GRED symptoms of the patient; a control unit for controlling the pulse generator 107 and a sensor adapted for sensing breathing signals from the patient; wherein the control unit is further adapted for synchronizing the pulse generator 107 in accordance with the breathing signals to thereby generating pulses only when the abdomen pressure is positive. According to some embodiments the pulse generator 107 is further configured for providing symmetric electrical stimulation bursts.

One other exemplary embodiment of the disclosed subject matter a device for treating gastroesophageal reflux disease (GERD) of a patient; the device comprises: a plurality of electrodes adapted to be placed in electrical contact with the skin of the abdomen; a pulse generator 107 for providing electrical stimulation signals to the electrodes; wherein the electrical stimulation bursts being for directing the stomach contents to creep up to the esophagus, to thereby causing unpleasant sensation leading to decrease the appetite for treating obesity or wherein the electrical stimulation bursts being for causing the stomach contents to creep down to the duodenum and to empty the stomach for treating paralysis of the stomach or wherein the electrical stimulation bursts being for causing the transverses colon contents to creep down to the sigmoid colon to thereby treating constipation; and a control unit 103 for controlling the pulse generator 107.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION OF THE INVENTION

Figure 1A:
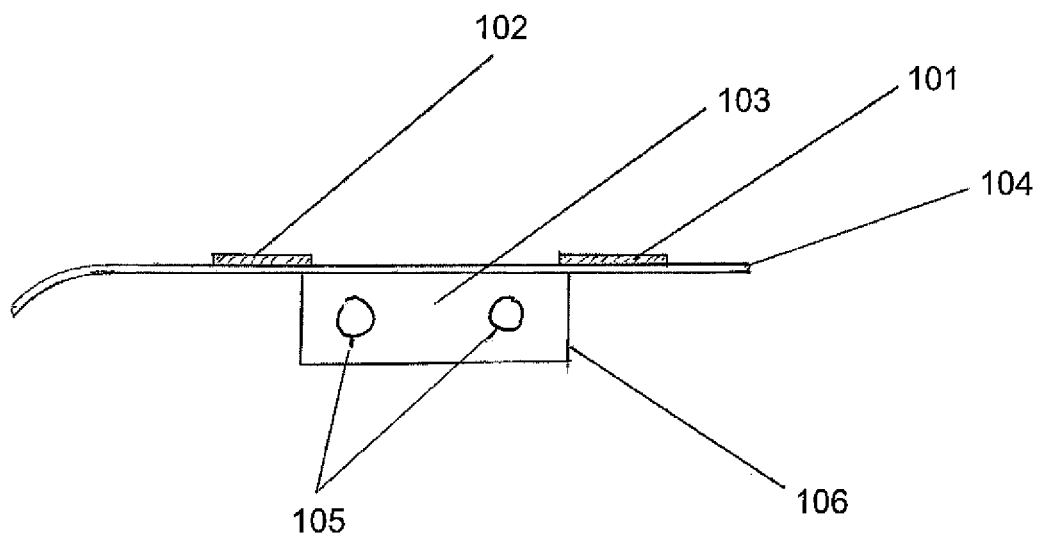
FIGS. 1A and 1B illustrate a device for treating the digestive system in accordance with some embodiments of the disclosed subject matter.
Figure 1B:
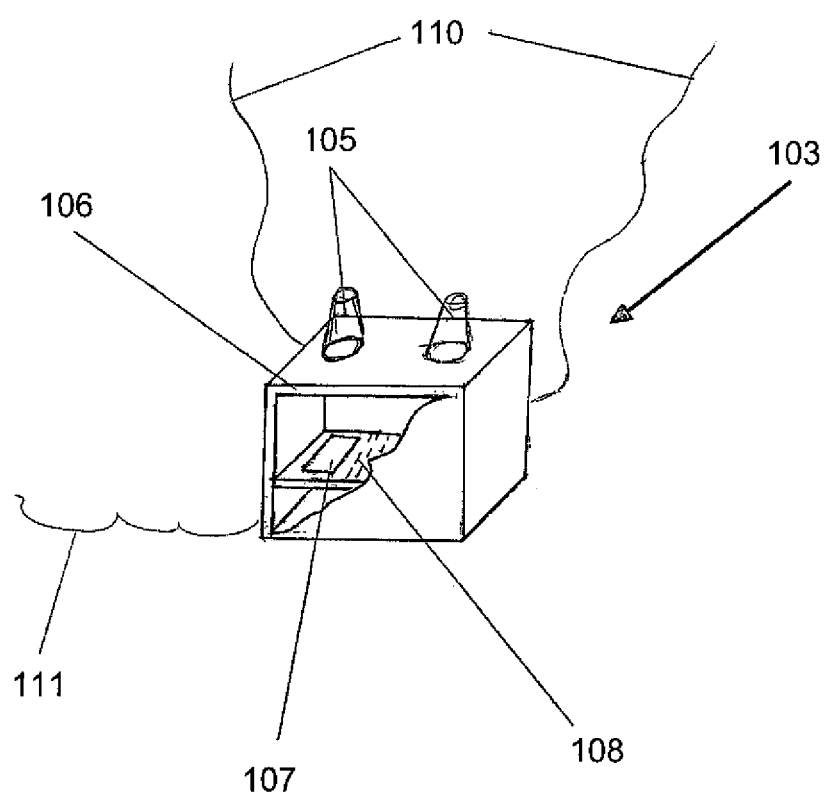

FIGS. 1*a* and 1*b* illustrate a device for treating the digestive, in accordance with some embodiments of the disclosed subject matter.

FIG. 1*a* is a top view of the device in accordance with some embodiments of the disclosed subject matter. The device (not shown in this figure) can be worn on the user body via adjustable belt and or pressure sensitive adhesive (PSA). The device (not shown in this figure) generates electrical pulses that are delivered to the user abdomen muscles via two or more electrodes. The device (not shown in this figure) includes a control unit 103, a control unit case 106, an adjustable belt 104 and a plurality of electrodes 101 and 102.

The control unit 103 includes the electric circuit (printed board) PCB and a battery or multiple batteries pack (not shown in this figure). The control unit 103 includes two or more keys or knobs 105 for turning on/off, selecting the required operation protocol and pulse parameters, and two (or more) LEDs (not shown) for status indication. The control unit 103 is explained in greater details in FIG. 1*b*. The adjustable belt (104) is adapted ensures comfortable and proper attachment of the device (not shown in this figure) to the user body and allows daily activities.

The control unit case 106 may be constructed to be adequately flexible in order to allow good fit with the user body.

The electrodes 101 and 102 are each adapted to be positioned in electrical conduct with the skin of selected regions of a patient abdomen. The electrodes 101 and 102 are replaceable and disposable; they are supplied to the user packed in a sealed watertight package. The electrode structure contains multiple layers that may include a substrate liner; polymer film (e.g. polyester) or foam (e.g. polyurethane) or nonwoven (e.g. polypropylene fibers) coated with conductive layer (e.g. a bland of silver silver-chloride or graphite or metal) and an aqueous conductive adhesive (e.g. conductive hydrogel or viscose layer with water). The electrodes are attached to the control unit side wall or integrated into the adjustable belt 104, and connected to the control unit 103 via special conductive wires 110. A siliconized film (release liner) protects the adhesive/hydrogel and is removed before use.

The electrodes 101 and 102 may be integrated (as shown this figure) or separated (as shown FIG. 3) from the device (not shown in the figure) and can be located in various locations of the user abdomen.

In order to allow daily operation through clothes there is an option to remotely control the device (not shown in this figure) by using a wire/wireless remote control unite or a special unit with magnet that magnetically operates the switches of the device.

FIG. 1*b* illustrates the control unit in accordance with some embodiments of the disclosed subject matter. The control unit 103 includes control keys 105, a case 106 and printed circuit board (PCB) 108. The PCB 108 includes microcontroller, digital circuits, memory, communication, high voltage circuits, analog circuits, high voltages switches and bridges, protection circuits (not shown) and the pulse generator 107. The control unit 103 is connected to the electrodes (not shown) with the electrodes conductive wires 110. The control unit 103 is in electrical contact with the sensors (not shown) via conductive wire 111. The control unit may be controlled by any remote control device with any type of communication.

Figure 2:
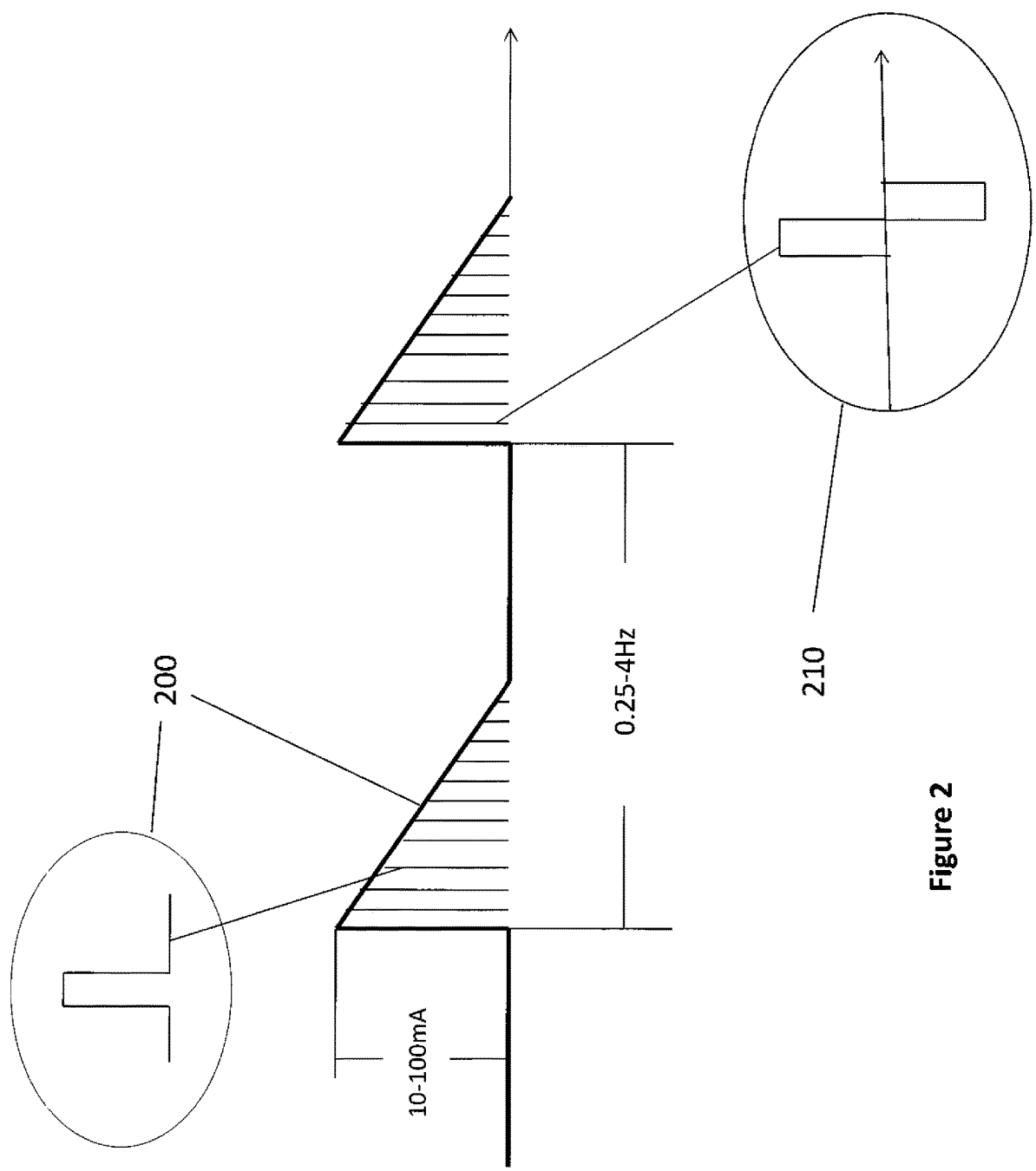
FIG. 2 illustrates an example of the asymmetrical burst stimulation monophasicpulses or half wave in case of biphasic pulses, in accordance with some embodiments of the disclosed subject matter.

FIG. 2 illustrates an example of the monophasic asymmetrical burst stimulation pulses 200 and the biphasic stimulation pulses 210, in accordance with some embodiments of the disclosed subject matter. In another embodiment, more types of asymmetrical burst and pulses may be used for example: skew nonlinear curves, asymmetrical stairs pulses.

Figure 3:
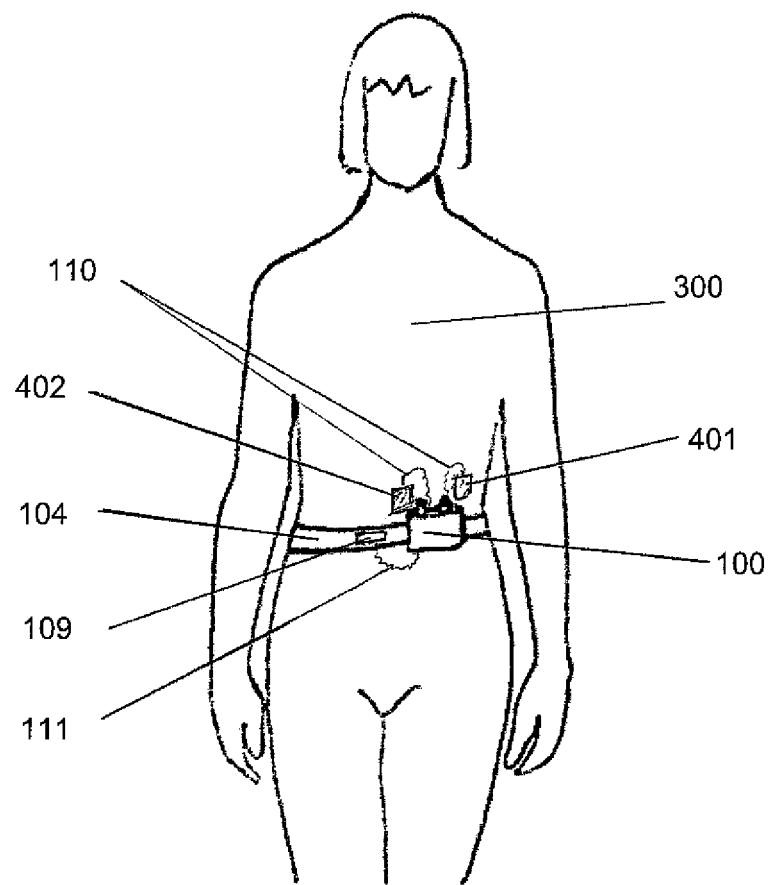
FIG. 3 is an illustration of user wearing the device on the abdomen, in accordance with some embodiments of the disclosed subject matter.

FIG. 3 is an illustration of user 300 wearing the device 100 on the abdomen, in accordance with some embodiments of the disclosed subject matter. The adjustable belt 104 is worn on the user 300. The adjustable belt 104 includes a sensor 109. The sensor 109 is connected to the control unit 103 via conductive wire (multiple wires cable) 111. The electrodes 401 and 402 are connected to the device 100 via conductive wires 110. The second electrode 402 or both electrodes 401 and 402 may be integrated (as shown in FIG. 1) or separated (as shown in this figure) from the device 100 and can be located in various locations of the user abdomen. This structure allows deeper penetration of the pulse current and may be required primarily by obese users with thick layer of fate that may prevent the current to reach the inner abdomen muscles.

Figure 4:
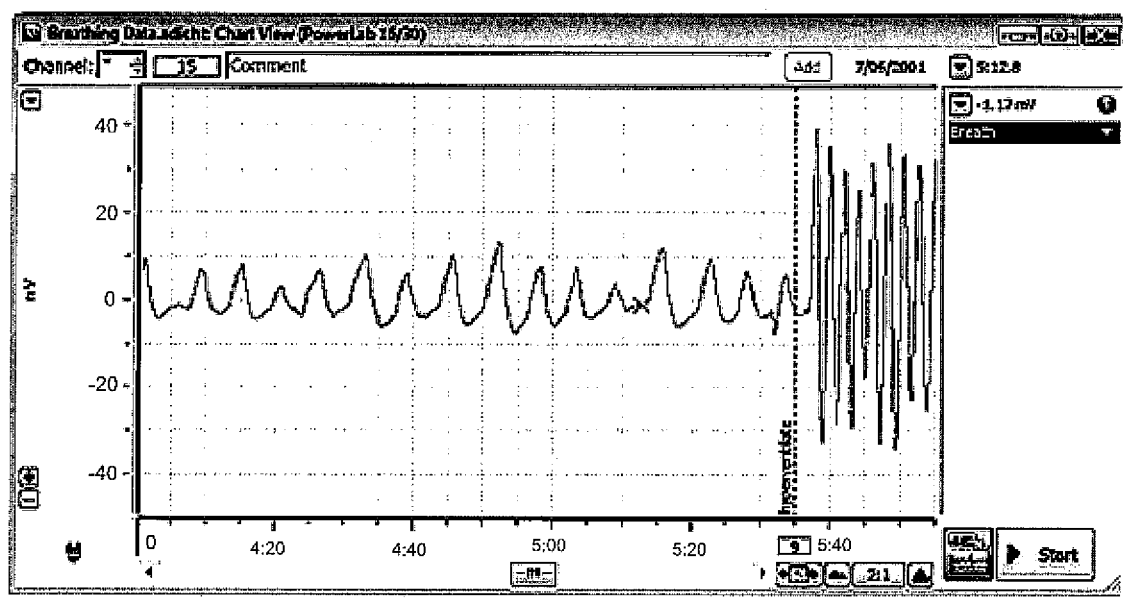
FIG. 4 is an illustration of typical data that is generated by a Piezoelectric Respiratory Belt Transducer, in accordance with some embodiments of the disclosed subject matter.

FIG. 4 is an illustration of typical data that is generated by a Piezoelectric Respiratory Belt Transducer, in accordance with some embodiments of the disclosed subject matter. The figure illustrates the change in voltage as a result of a change in thoracic or abdominal circumference due to respiration. By measuring the voltage change the device synchronizes the pulses generation with breathing rate. Pulses are generated during the periods of positive values.

Figure 5:
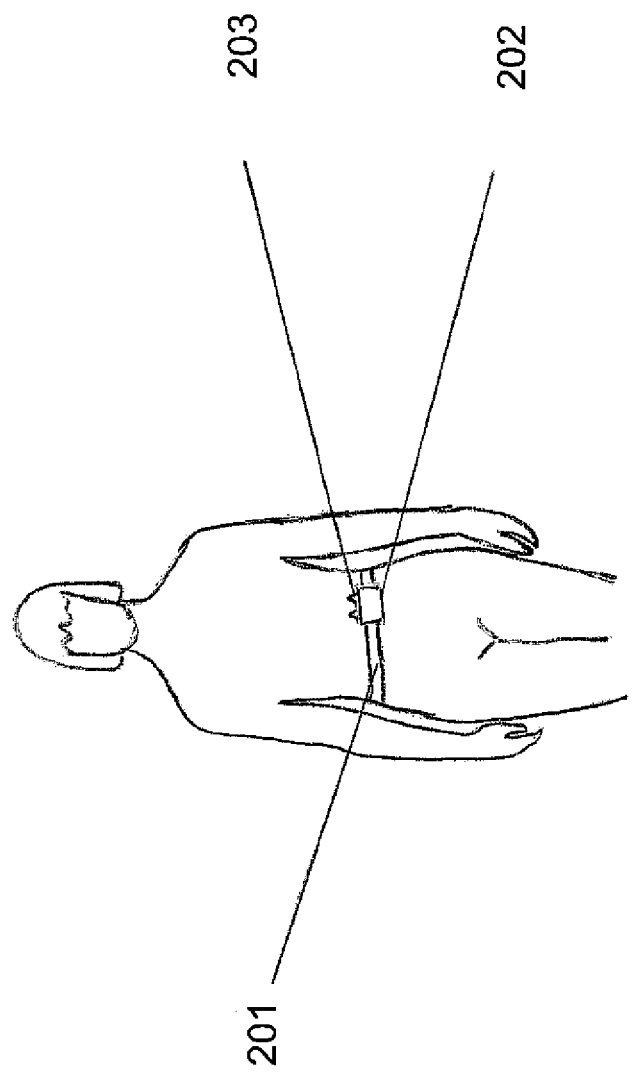
FIG. 5 is an illustration of a subject wearing, on the abdomen, a device with a pulse motion mechanism, in accordance with some embodiments of the disclosed subject matter.

FIG. 5 is an illustration of a subject wearing, on the abdomen, a device with a pulse motion mechanism, in accordance with some embodiments of the disclosed subject matter. According to some embodiments the dynamic motions of the abdomen are created by a pulse motion mechanism 202 which is mounted on a belt 201 that is worn on the subject 200. When the subject 200 wears the belt, the mechanism is positioned onto a selected region or regions of the patient abdomen. The mechanism 202 extends and releases sequentially (alternatively inflates and deflates) causing the abdomen wall to follow its movements. The mechanism 202 is activated by a suitable electrical current pattern (to create the required motion) that is generated by the control unit 203. The mechanism 202 may be synchronized with the patient body signals.

Figure 6:
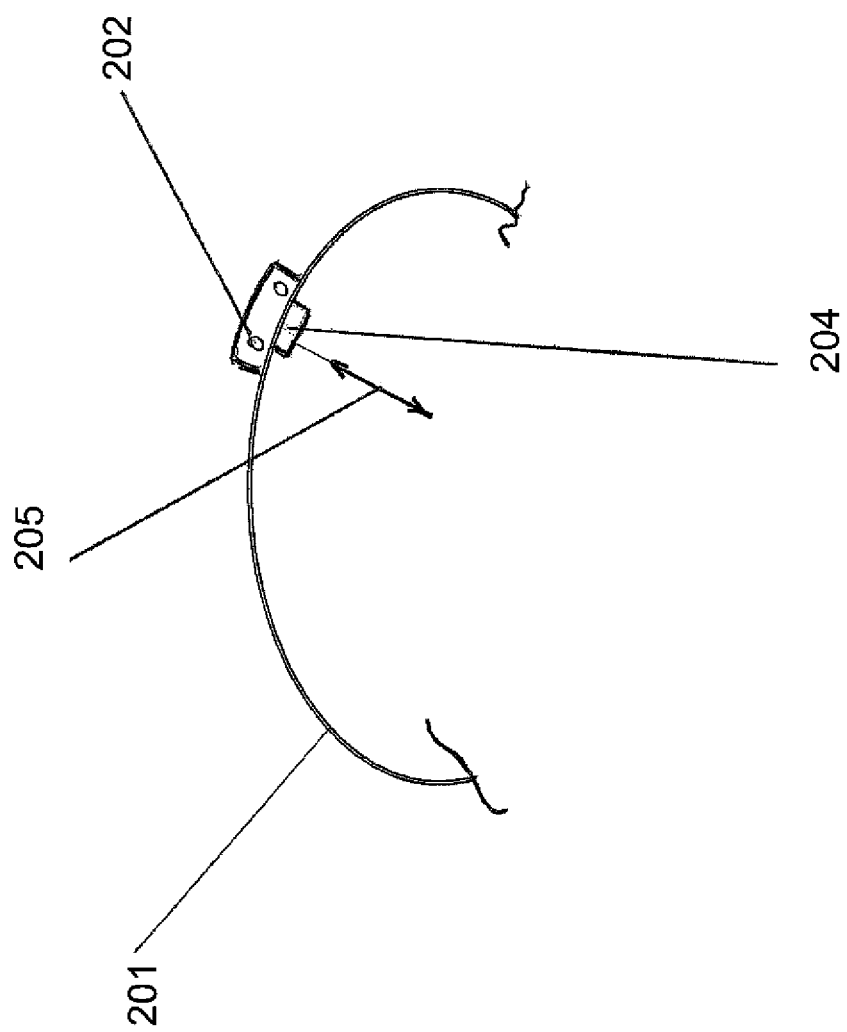
FIG. 6 is a top view illustration of a device with a pulse motion mechanism, in accordance with some embodiments of the disclosed subject matter.

FIG. 6 is a top view illustration of a device with a pulse motion mechanism, in accordance with some embodiments of the disclosed subject matter. The pulse motion mechanism 202 may include, for example, an electrical linear actuator or a Rotary actuator with an eccentric arm, both can drive a piston 204. The pulse motion mechanism 202 may also include an air bag (204). The piston 204 expands and releases in sequence. The air bag 204 sequentially inflates and deflates and is coupled with an electrical air pump and an air valve. The power may be supplied by a battery that is mounted in the control unit (not shown in the figure). Arrow 205 shows the direction of the movement of the piston or an air bag (204).

Figure 7A:
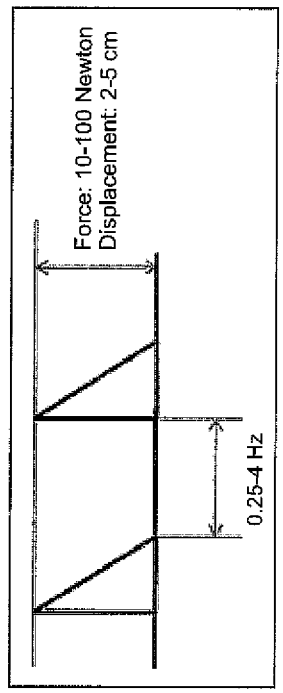
FIG. 7A to 7C illustrate a force and displacement pulse pattern of the device, in accordance with some embodiments of the disclosed subject matter.
Figure 7B:
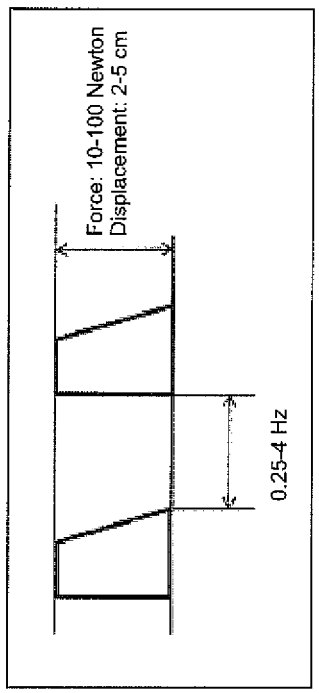
Figure 7C:
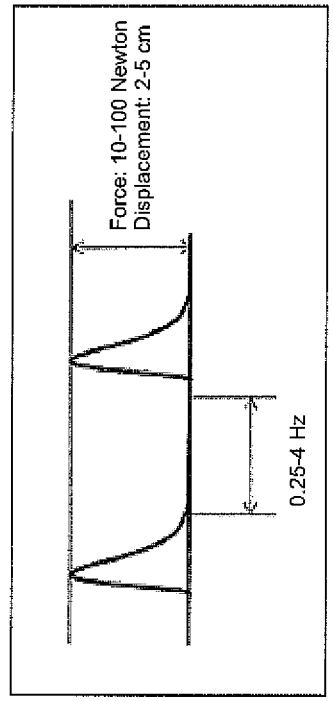

FIG. 7 illustrates force and displacement pulse patterns of the device with a pulse motion mechanism, in accordance with some embodiments of the disclosed subject matter. The resulting force and displacement pulse pattern includes sequential saw teeth pattern 701, asymmetric trapezoidal pattern 702 and skewed sinusoidal pattern 703. It should be noted that the pattern may also include symmetrical rectangle pattern or symmetrical sinusoidal pattern (not shown in the figure).

We claim:

1. A non-invasive method for treating gastroesophageal reflux disease (GERD) in a patient, the method comprising: positioning a plurality of electrodes in electrical contact with the skin of a target region of the abdomen of the patient; and applying a series of electrical symmetrical bursts to said electrodes to generate contractions of abdominal muscles thereby generating movements of a digestive system of said patient wherein said movements are for causing the content of the esophagus to return to the stomach and to relieve GERD symptoms of said patient.

2. The method according to claim 1, further comprising synchronizing said pulses with one or more body signals of the patient, wherein said one or more body signals are selected from the group consisting of: breathing, heart pulse, monotony movements and body position.

3. The method according to claim 2, wherein said symmetrical bursts are modulated biphasic symmetrical pulses.

4. A non-invasive device for treating the digestive system symptoms of a patient, the device comprising: a plurality of electrodes in electrical contact with the skin of a target region of the abdomen of the patient; a pulse generator for providing symmetrical modulated bursts of pulses to said electrodes, wherein said modulated symmetrical burst of pulses are for stimulating the abdomen muscles and for moving the digestive system, wherein said moving being for treating a digestive symptom or a disease; a control unit for controlling said pulse generator, wherein a maximum voltage range of said pulses is +300V, a maximum current range is 150 mA, a pulse frequency range is 10 Hz-100 Hz, and a burst frequency range is 0.1-10 Hz; and a sensor connectable to said control unit, wherein said sensor is adapted for sensing one or more body signals of the patient wherein said one or more body signals are selected from a group consisting of: breathing, heart pulse, monotony movements and body position, wherein said control unit is further adapted for synchronizing said pulse generator in accordance with said one of more body signals to improve effectiveness of said electrical stimulation.

5. The device according to claim 4, wherein said symmetrical bursts are modulated biphasic symmetrical pulses.

6. The device according to claim 4, wherein said digestive system symptom or said disease are selected from the group consisting of gastroesophageal reflux disease (GERD), Gastroparesis and Constipation.

7. The device according to claim 4, wherein said sensor is selected from at least one of a piezoelectric respiratory belt transducer for sensing breathing rate, an ECG for sensing heartbeat, an accelerometer and a gyro for sensing body movements.

8. A non-invasive device for treating digestive system of a patient, the device comprising:
   a plurality of electrodes adapted to be placed in electrical contact with the skin of a target region of the abdomen of said patient;
   a pulse generator configured for providing symmetric electrical stimulation bursts to said electrodes to generate symmetrical contractions of abdominal muscles of said abdomen; thereby generating movements of a digestive system of said patient wherein said movements are for causing content of the esophagus to return to the stomach and to relieve one member selected from a group consisting of gastroesophageal reflux (GERD) symptoms, Gastroparesis and Constipation of said patient.

9. The device of claim 8 further comprising a control unit configured for controlling said pulse generator and a sensor adapted for sensing breathing signals from said patient; wherein said control unit is further adapted for synchronizing said pulse generator in accordance with said breathing signals to generate pulses only when the abdomen pressure is positive.

10. A non-invasive device for treating gastroesophageal reflux disease (GERD) in a patient, the device comprising:

a plurality of electrodes adapted to be placed in electrical contact with the skin of a target region of the abdomen of the patient; and a pulse generator configured for providing a series of electrical symmetrical bursts to said electrodes to generate contractions of abdominal muscles thereby generating movements of a digestive system of said patient wherein said movements are for causing the content of the esophagus to return to the stomach and to relieve GERD symptoms of said patient.

* * * * *